(12) United States Patent
Henriot et al.

(10) Patent No.: US 6,871,118 B2
(45) Date of Patent: Mar. 22, 2005

(54) METHOD FOR DETECTING AND CONTROLLING HYDRATE FORMATION AT ANY POINT OF A PIPE CARRYING MULTIPHASE PETROLEUM FLUIDS

(75) Inventors: Véronique Henriot, Rueil Malmaison (FR); Véronique Lachet, Meudon La Floret (FR); Eric Heintze, Meudon (FR)

(73) Assignee: Institut Francais Du Petrole, Rueil Malmaison Cedex (FR)

( * ) Notice: Subject to any disclaimer, the term of this patent is extended or adjusted under 35 U.S.C. 154(b) by 206 days.

(21) Appl. No.: 10/080,682

(22) Filed: Feb. 25, 2002

(65) Prior Publication Data

US 2002/0166818 A1 Nov. 14, 2002

(30) Foreign Application Priority Data

Mar. 1, 2001 (FR) .......................................... 01 02842

(51) Int. Cl.[7] .................... G05B 21/00; G05D 11/00; G05P 7/00; G01N 35/00; G01N 25/18
(52) U.S. Cl. .................... 700/266; 422/50; 422/68.1; 422/81; 422/82.12; 436/43; 436/147; 436/149; 436/150; 700/278; 700/282; 700/299; 702/127; 702/130; 702/136
(58) Field of Search .................... 422/50, 68.1, 81, 422/82.12; 702/127, 130, 136; 700/266, 278, 282, 299; 436/43, 147, 149, 150

(56) References Cited

U.S. PATENT DOCUMENTS

| | | | |
|---|---|---|---|
| 5,426,258 A | * 6/1995 | Thomas et al. | ................ 585/15 |
| 5,550,761 A | * 8/1996 | Pauchon et al. | ................ 703/9 |
| 5,960,187 A | * 9/1999 | Faille et al. | ................ 703/12 |
| 6,028,992 A | 2/2000 | Henriot et al. | .......... 395/500.3 |
| 6,155,102 A | * 12/2000 | Toma et al. | ................ 73/61.44 |
| 6,656,366 B1 | * 12/2003 | Fung et al. | ................ 210/737 |

FOREIGN PATENT DOCUMENTS

| | | | |
|---|---|---|---|
| FR | 2 687 223 | 2/1992 | .......... G01N/11/14 |
| WO | 96/32629 | 10/1996 | .......... G01N/11/08 |
| WO | 9845692 | 10/1998 | .......... G01N/27/00 |

OTHER PUBLICATIONS

Henriot, et al.; "Tacite: Contribution of Fluid Composition Tracking on Transient Multiphase Flow Simulation"; Petroleum and Techniques, French Association of Petroleum Engineers, Paris, France, No. Suppl 408, May 1, 1997; pps. 1–10.

(List continued on next page.)

Primary Examiner—Jill Warden
Assistant Examiner—Brian Sines
(74) Attorney, Agent, or Firm—Antonelli, Terry, Stout & Kraus, LLP (57) ABSTRACT

Method intended for continuous detection and control of hydrate formation at any point of a pipe carrying multiphase petroleum fluids. The method uses a compositional code allowing to simulate the circulation modes and conditions at any point of the pipe, considering that the fluid mixture is substantially continuously at equilibrium, that the composition of the multiphase mixture is variable all along the pipe and that the mass of each constituent of the mixture is globally defined by a mass conservation equation regardless of its phase state. The thermodynamic hydrate formation conditions are detected after a particular stage of grouping the petroleum fluids into pseudo-components so as to isolate the hydrate forming components, with definition for each one of a mass fraction and of a certain number of characteristic physical quantities, and the data relative to these particular fractions are applied to the modules so as to determine at any point the hydrate dissociation temperature (Td). A control device (C) can also be used to compare the temperature of the petroleum fluids with this dissociation temperature (Td), and measures designed to fight hydrate formation can be applied under the control of this control device (C). The method can be applied for deep-sea petroleum production for example.

5 Claims, 7 Drawing Sheets

OTHER PUBLICATIONS

Duret, et al.; "Pipeline Bundles Model Implemented Into a Multiphase Flow Model", Society of Petroleum Engineers Inc. 6248, Annual technical Conference and Exhibition; Dallas, Texas, Oct. 1–4, 2000, pps. 1–7.

Danesh, et al.; "Hydrate Equilibrium Data of Methyl Cyclopentane with Methane or Nitrogen", Chemical Engineering Research and Design, Part A, Institution of Chemical Engineers, vol. 72, Mar. 1, 1994, pps. 197–200.

Calange, et al.; "Onset Crystallization Temperature and Deposit Amount For Waxy Crudes: Experimental Determination and Thermodynamic Modelling", SPE International Sysposium on Oilfield Chemistry, Feb. 18, 1997, pps. 283–290.

* cited by examiner

METHOD FOR DETECTING AND CONTROLLING HYDRATE FORMATION AT ANY POINT OF A PIPE CARRYING MULTIPHASE PETROLEUM FLUIDS

FIELD OF THE INVENTION

The present invention relates to a method for detecting and controlling hydrate formation at any point of a pipe carrying multiphase petroleum fluids.

BACKGROUND OF THE INVENTION

Producing hydrocarbons from deep-sea reservoirs (1500–3000 m) raises a great variety of difficulties, mainly because of the high pressures and low temperatures prevailing at such depths. These difficulties are encountered in all the spheres of petroleum expertise: drilling and well servicing, process facilities (FPSO, FWHP, etc.) and their anchor systems, subsea technologies (multiphase pumping, subsea separation of petroleum fluid phases), risers and umbilicals or flow assurance.

As regards production proper, the operator is bound to give flow assurance despite many obstacles such as slugging, mineral or organic deposits, or hydrate formation. In the case of deep offshore drilling, hydrate formation is favoured by higher pressures and lower temperatures. Production stops during which the fluids cool down increase the hydrate formation risks still more.

Late detection of the presence of hydrates, notably through ignorance of the conditions of their formation in pipes, can lead to costly production problems: complete clogging of the production and/or transport pipes. It is therefore important for the operator to have means allowing to assess risks of any nature so as to implement control and servicing techniques and thus to be able to guarantee good flow of the circulating fluids.

In order to protect and thermally insulate subsea pipes, they are housed in an external tube withstanding the hydrostatic pressure. Most often, several pipes are grouped together so as to form bundles. These grouped pipes often have different functions. They are used for hydrocarbon production, injection of fluids into the reservoir, gas lift, circulation of heating fluid, etc. A low thermal conductivity lagging left at atmospheric pressure or under vacuum, with separations positioned at regular intervals for safety reasons, is for example interposed in the space between them.

With an efficient tool allowing continuous assessment of the risk of hydrate formation or of other deposits, the operator can take action by means of either pipe heating or additive injection. However, such a tool is difficult to set up and costly in calculating time, especially if the detailed composition of the petroleum fluids has to be taken into account. In order to study their behaviour more easily, it is well-known to describe them as a combination of a number of components or pseudo-components much smaller than the real number of constituents. This combination is referred to as a grouped composition as opposed to a detailed composition.

Patents FR-2,753,535 and FR-2,806,803 filed by the applicant describe methods for predicting the temperatures at which appear deposits such as waxes or paraffins in petroleum crudes whose constituents are grouped or lumped together into a smaller number of pseudo-components representing each several hydrocarbon classes and whose physico-chemical parameters are determined by combining the corresponding parameters of a certain number of pure hydrocarbons grouped together in a database. The pseudo-components of this grouped formulation are applied to a thermodynamic module allowing to determine various parameters indicative of the deposit formation conditions.

Various simulation softwares available on the market allow to model the behaviour of multiphase fluids circulating in pipelines.

The following patents or patent applications: U.S. Pat. No. 5,550,761, FR-2,756,044 (U.S. Pat. No. 6,028,992) and FR-2,756,045 (U.S. Pat. No. 5,960,187), FR-00/08,200 and FR-00/09,889 filed by the applicant, and the following publications:

Faille I. and Heintzé E., <<A rough finite volume scheme for modeling two-phase flow in a pipeline>>, Computers & Fluids 28 (1999), and Pauchon C. et al., <<TACITE: a comprehensive mechanistic model for two-phase flow>>, $6^{th}$ BHRG Multiphase International Conference, Cannes, France, June (1993)

notably describe the TACITE (registered trade name) simulation code which simulates the transient behaviour of circulating multiphase fluids by continuously taking their composition into account. With such a predictive code, the production engineer can define the characteristics of fluid (notably hydrocarbon) transport systems: pipes, separators, valves, control systems, etc. One of the main goals of these simulation operations is to precisely predict the characteristics of transient flows in situations such as: inflow rate variation, pressure drop at the outlet, production stop and restart, pigging, appearance and propagation of slugs, formation of deposits likely to form under certain thermodynamic conditions, etc.

The flow modes of multiphase fluids in tubes are extremely varied and complex. Two-phase flows, for example, can be stratified, the liquid phase flowing in the lower part of the pipe, or intermittent with a succession of liquid and gas slugs, or disperse, the liquid being carried along in form of fine droplets. The flow mode and slippage between the phases vary notably with the inclination of the pipes to the horizontal and depend on the flow rate, the temperature, etc.

It can be reminded that the TACITE code allows to follow the composition variations of hydrocarbon mixtures. As already described in the aforementioned patents filed by the applicant, there is a mass conservation equation for each pseudo-component. There also is a momentum equation and an equation for the energy of the mixture. The corresponding equations are reminded hereafter, after a definition of the symbols and notations:

V absolute phase velocity

U surface velocity

R volume fraction per phase $\rho$ phase density

H phase enthalpy

E internal energy

P pressure of the mixture $T_w$ wall friction $Q_w$ wall heat flow between the pipeline and the surrounding medium $\theta$ pipeline inclination g gravity S pipeline section x mass fraction of the component in a given phase p number of phases (1 to 3)

N number of components
k phase index
i component index
m mixture index

The mass equilibrium equation for each component is:

$$\frac{\partial}{\partial t}\left\{\sum_{k=1}^{P} S(\rho_k R_k x_i^k)\right\} + \frac{\partial}{\partial x}\left\{\sum_{k=1}^{P} S(\rho_k R_k x_i^k V_k)\right\} = \qquad (1)$$

$$0 \; (i=1,\cdots,N).$$

The momentum equilibrium equation of the mixture is:

$$\frac{\partial}{\partial t}\left\{\sum_{k=1}^{P} S(\rho_k R_k V_k)\right\} + \frac{\partial}{\partial x}\left\{\left(\sum_{k=1}^{P} S(\rho_k R_k V_k^2)\right) + P\right\} = \qquad (2)$$

$$S(T_w - \rho_m g \sin\theta).$$

The mixture energy equilibrium equation is:

$$\frac{\partial}{\partial t}\left\{\sum_{k=1}^{P} S(\rho_k E_k)\right\} + \frac{\partial}{\partial x}\left\{\sum_{k=1}^{P} S(\rho_k R_k V_k H_k)\right\} = \qquad (3)$$

$$S(Q_w - \rho_m g U_m \sin\theta).$$

Numerical Scheme

The numerical scheme is conservative and non-dissipative. It provides a good mass and energy balance at any point of the pipe and at any time. A mixed implicit/explicit scheme is used to optimize the computing time and the capacity of following the void fraction wave fronts, which is particularly important when the configuration of the terrain followed by the pipeline or its own configuration favours the formation of liquid slugs with propagation of void waves in the two opposite directions of the pipeline, phenomena commonly referred to by specialists as terrain slugging or severe slugging.

Thermodynamic Module

The TACITE simulation code comprises an integrated thermodynamic flash module, i.e. an integrated subprogram intended to compute the thermodynamic properties (liquid-vapour equilibrium, composition of each phase) by means of an equation of state. This flash carries out two-phase and three-phase thermodynamic equilibrium computations for hydrocarbon mixtures including water. The Peng-Robinson (1) and Soave-Redlich-Kwong (2) cubic equations of state are used for modelling the thermodynamic properties at phase equilibrium. These equations are defined in the following publications:

Peng D. Y. et al., <<A new two-constant equation of state>>, Ind. Eng. Chem Fund. 15, 59 (1976), Soave G., <<Equilibrium constants from a modified Redlich-Kwong equation of state>>, Chem. Eng. Sci. 27, 1197 (1972).

In both cases, the molecular volumes can be corrected by the Peneloux method described in the following publication:

Péneloux A. et al., <<A consistent correction for Redlich-Kwong-Soave volumes>>, Fluid Phase Equilibria 8, 7 (1982).

The module referred to as flash allows precise monitoring of the composition of the fluids, in space as well as in time, throughout the simulation.

This composition monitoring makes the TACITE code particularly well-suited for precise prediction of the hydrate formation risk, as described below.

Hydrodynamic Module

The hydrodynamic module computes the flow regime, the phase slip velocity and the friction terms.

SUMMARY OF THE INVENTION

The method according to the invention allows continuous detection, at any point of a pipe carrying a multiphase mixture of petroleum fluids, of the thermodynamic conditions of hydrate formation. It comprises using a mechanistic hydrodynamic module and an integrated compositional thermodynamic module for defining the phase properties and solving mass conservation equations, momentum conservation equations and equations of energy transfer in the mixture, considering that the mixture of fluids is substantially continuously at equilibrium, that the composition of the multiphase mixture is variable all along the pipe and that the mass of each constituent of the mixture is globally defined by a mass conservation equation regardless of its phase state. The petroleum fluids are lumped into a limited number of pseudo-components comprising each certain hydrocarbon fractions.

The method is characterized in that the thermodynamic conditions of hydrate formation are detected after particular lumping of the petroleum fluids into pseudo-components so as to isolate the hydrate forming components, with definition for each one of them of a mass fraction and of a certain number of characteristic physical quantities, and data relative to these selected pseudo-components are applied to the thermodynamic and hydrodynamic modules so as to determine at any point the hydrate dissociation temperature (Td).

The invention also relates to a method allowing continuous control, at any point of a pipe carrying multiphase petroleum fluids, of the formation of hydrates. It comprises detecting the thermodynamic conditions of hydrate formation as defined above, using a control device for comparing the temperature of the petroleum fluids with this dissociation temperature (Td) and applying, under the control of this control device, measures designed to fight hydrate formation.

According to a first implementation mode, heating means associated with the pipe are used to raise the temperature of the petroleum fluids above the dissociation temperature. When the pipe is included with at least a second pipe in a tube isolated from the outside environment, the second pipe is used for circulation of a warm fluid.

According to a second implementation mode, hydrate inhibitors are injected into the pipe under the control of control device (C).

BRIEF DESCRIPTION OF THE DRAWINGS

Other features and advantages of the method according to the invention will be clear from reading the description hereafter of a non-limitative example, with reference to the accompanying drawings wherein.

DETAILED DESCRIPTION

Presentation of the Thermodynamic Module

Structure of Hydrates

Hydrates are solid compounds consisting of hydrocarbon molecules (methane, ethane, carbon dioxide, etc.) trapped at high pressure and low temperature in approximately spherical cages formed by a three-dimensional crystal lattice of water molecules. This structure is metastable in the absence of hydrocarbons and requires a minimum filling ratio to ensure its stabilization. Unlike the crystal lattice of ice, the crystal lattice of hydrates can remain stable above 0° C.

X-ray diffraction measurements carried out in the fifties have highlighted two crystal structures of hydrates according to the nature of the insertion molecules present. In both cases, these structures are cubic structures organized in networks of small and large cavities. The table hereafter shows the possible occupation of the various cavities according to the nature of the hydrate forming molecules involved (+: possible occupation of the cavity by the molecule; −: cavity size insufficient to contain the molecule).

| Molecules | Structure I | | Structure II | |
|---|---|---|---|---|
| | Small cavity | Large cavity | Small cavity | Large cavity |
| $N_2$ | + | + | + | + |
| $CO_2$ | + | + | + | + |
| $H_2S$ | + | + | + | + |
| $C_1$ | + | + | + | + |
| $C_2$ | − | + | − | + |
| $C_3$ | − | − | − | + |
| $iC_4$ | − | − | − | + |
| $nC_4$ | − | − | − | + |

The lattice of structure I is a face-centred cubic type system. Each mesh contains 46 water molecules organized in:

2 small cavities with a radius of 3.95 Å, 6 large cavities with a radius of 4.33 Å.

The crystal of structure II has a diamond-shaped lattice. Each mesh contains 136 water molecules and 24 cavities:

16 small cavities with a radius of 3.91 Å, 8 large cavities with a radius of 4.73 Å.

A third structure, the H structure, has also been identified. Its crystal lattice, of hexagonal type, consists of 34 water molecules and 6 cavities:

2 small cavities with a radius of 3.91 Å, 3 medium cavities with a radius of 4.06 Å, 1 large cavity with a radius of 5.71 Å.

The latter structure is much rarer than the two others, it is mainly encountered in the case of cyclic alkanes or alkenes.

Thermodynamics of Phase Equilibrium in the Presence of Hydrates

Any hydrate prediction computation is based on the criterion of water equilibrium in the hydrate phase and in the aqueous phase, i.e. on the equality of the chemical potential of water in the hydrate phase and of the chemical potential of water in the aqueous phase:

$$\mu_{eau}^{aqueuse}(P,T) = \mu_{eau}^{hydrate}(P,T). \quad (1)$$

According to Van der Waals and Platteeuw's statistical theory described in the following publication: Van der Waals, J. H., et al., <<Clathrate Solutions>>, Adv. Chem. Phys., 2, 1 (1959), the chemical potential of water in the hydrate phase can be written as follows:

$$\mu_{eau}^{hydrate}(P, T) = \mu_{eau}^{hydrate-vide}(P, T) + RT \sum_i v_i \ln\left(1 - \sum_k \theta_{ik}\right), \quad (2)$$

with:

$\mu_{water}^{hydrate-void}$: chemical potential of water in the crystal lattice in the absence of hydrocarbon molecule, $v_i$: ratio of the number of cavities of type i (small or large) to the number of water molecules in a single crystal, $\theta_k$: probability of a cavity of type i being occupied by a hydrocarbon molecule of type k. According to Langmuir's adsorption theory, this probability can be calculated by:

$$\theta_{ik} = \frac{C_{ik}f_k}{1 + \sum_j C_{ij}f_j}, \qquad (3)$$

where $f_k$ is the fugacity of component k and $C_{ik}$ is Langmuir's coefficient of adsorption of a molecule k in a cavity of type i.

Langmuir's coefficients can be expressed from the potential of interaction between the water molecules and the gas molecules included in the cavities of the hydrate crystal structure:

$$C_{ik} = \frac{4\pi}{kT}\int_0^R \exp\left(\frac{-W(r)}{kT}\right)r^2\,dr, \qquad (4)$$

where k is the Boltzmann constant and W(r) the potential energy of interaction between the water molecules forming the cavity and the gas molecules lying at a distance r from the centre of the cavity. There are several forms of potential, the most commonly used forms are the Lennard-Jones potential the Kihara potential and the square sink potential.

The Lennard-Jones potential between two molecules is written as follows:

$$W(r) = 4\varepsilon\left[\left(\frac{\sigma}{r}\right)^{12} - \left(\frac{\sigma}{r}\right)^6\right], \qquad (5)$$

with:
ε: depth of the sink,
r: distance between the centres of the molecules,
σ: exclusion diameter, r such that W(σ)=0.

The Kihara potential is similar to the Lennard-Jones potential, but the molecules are considered to be spheres of non-zero radius. Its analytical expression is as follows:

$$\begin{aligned} W(r) &= \infty & \text{if } r \leq 2a \\ W(r) &= 4\varepsilon\left[\left(\frac{\sigma}{r-2a}\right)^{12} - \left(\frac{\sigma}{r-2a}\right)^6\right] & \text{if } r > 2a \end{aligned} \qquad (6)$$

with:
ε: depth of the sink,
σ: such that W(σ+2a)=0,
a: mean radius of the 2 molecules,
r: distance between the centres of the molecules.

Finally, the square sink potential is given by:

$$W(x) = \infty \text{ si } 0 \leq x < \sigma$$
$$W(x) = -\varepsilon \text{ si } \sigma \leq x \leq \alpha\sigma \qquad (7)$$
$$W(x) = 0 \text{ si } x > \alpha\sigma$$

The various parameters which appear in the expressions of these potentials are adjusted to experimental hydrate equilibrium data.

The chemical potential of water in the aqueous phase is written as follows:

$$\mu_{eau}^{aqueuse}(P,T) = \mu_{eau}^0(P,T) + RT\ln(\gamma x), \qquad (8)$$

where γ is the activity coefficient of water, x the mole fraction of water in the aqueous phase and $\mu_{water}^0(P,T)$ the chemical potential of pure water. The effects of salts and of alcohols are taken into account, among other things, in this computation of the activity of water in the aqueous phase.

By equalizing Equations (2) and (8), the required equilibrium condition (1) is written as follows:

$$\mu_{eau}^0(P,T) - \mu_{eau}^{hydrate-vide}(P,T) = \qquad (9)$$
$$RT\sum_i v_i \ln\left(1 - \sum_k \theta_{ik}\right) - RT\ln(\gamma x).$$

By fixing the pressure, this equation allows to obtain the equilibrium temperature or conversely, by fixing the temperature we obtain the equilibrium pressure.

The various hydrate prediction modules are all based on the formalism described above. These modules differ essentially in the selection of the water-hydrocarbon interaction potential, in the selection of the equation of state used to compute the fugacities and in the module used to compute the activity of water in the liquid phase. We present more precisely hereafter the module that we have adapted for the purpose of TACITE.

Module Implemented in TACITE

The hydrate prediction module implemented in TACITE is inspired by Munck's model as described by Munck, J. et al., <<Computations of the formation of gas hydrates>>, Chem. Eng. Sci. 43, 2661 (1988). It allows to compute the dissociation temperature of hydrates at a given pressure in the case of a gas, of a liquid or of a two-phase gas-liquid mixture in contact with liquid water.

Langmuir Constants:

This module uses a square sink type potential W(r), which leads to an expression of the Langmuir constant of compound k in a cavity of type i as follows:

$$C_{ik} = \frac{A_{ik}}{T}\exp\left(\frac{B_{ik}}{T}\right). \qquad (10)$$

The values of parameters A and B of the various compounds forming hydrates are given in the table hereafter:

| | | Small cavity | | Large cavity | |
|---|---|---|---|---|---|
| Molecule | Structure | A × 10³ (K/atm) | B (K) | A × 10³ (K/atm) | B (K) |
| $N_2$ | I | 1.617 | 2905 | 6.078 | 2431 |
| | II | 0.1742 | 3082 | 18.00 | 1728 |
| $CO_2$ | I | 0.2474 | 3410 | 42.46 | 2813 |
| | II | 0.0845 | 3615 | 851.0 | 2025 |
| $H_2S$ | I | 0.0250 | 4568 | 16.34 | 3737 |
| | II | 0.0298 | 4878 | 87.2 | 2633 |
| $C_1$ | I | 0.7228 | 3187 | 23.35 | 2653 |
| | II | 0.2207 | 3453 | 100.0 | 1916 |
| $C_2$ | I | 0.0 | 0.0 | 3.039 | 3861 |
| | II | 0.0 | 0.0 | 240.0 | 2967 |
| $C_3$ | II | 0.0 | 0.0 | 5.455 | 4638 |
| $iC_4$ | II | 0.0 | 0.0 | 189.3 | 3800 |
| $nC_4$ | II | 0.0 | 0.0 | 30.51 | 3699 |

Computation of the Fugacities:

The fugacities of the various constituents present in the mixture, hydrate forming or not, are computed by means of the aforementioned Soave-Redlich-Kwong equation of state. Such a computation involves the fixed pressure and temperature flash module included in TACITE.

Activity of Water in the Aqueous Phase:

The Munck module disregards the solubility in the aqueous phase of hydrocarbons, nitrogen and hydrogen sulfide. On the other hand, the solubility of carbon dioxide in water cannot be disregarded, and it is computed by means of Henry's constant of $CO_2$ in water:

$$x_{CO_2} = \frac{f_{CO_2}}{H_{CO_2}}, \quad (11)$$

where $x_{CO2}$ is the mole fraction of $CO_2$ in the aqueous phase, $\theta_{CO2}$ the fugacity of $CO_2$ and $H_{CO2}$ Henry's constant of $C_{O2}$ in water, given by:

$$\ln H_{CO_2} = H_A + \frac{H_B}{T} + H_C \ln T + H_D T. \quad (12)$$

The values of the coefficients used to compute Henry's $CO_2$ constant are given in the table hereunder.

| $H_A$ (atm) | $H_B$ (atm · K) | $H_C$ (atm/lnK) | $H_D$ (atm · K$^{-1}$) |
|---|---|---|---|
| 160.27 | −8764.5 | −21.726 | $1.1055 \cdot 10^{-4}$ |

Reference Constants:

The chemical potential difference between pure liquid water and water in the hydrate-void phase (first member of Equation (9)) can be written as follows, with certain approximations:

$$\frac{\mu_{eau}^{hydrate-vide}(P,T) - \mu_{eau}^0(P,T)}{RT} = \quad (13)$$

$$\frac{\Delta\mu_0}{RT_0} - \int_{T_0}^{T} \frac{\Delta H_0 + \Delta C_p(T-T_0)}{RT^2} dT + \int_{P_0}^{P} \frac{\Delta V}{R\bar{T}} dP.$$

In this equation, $\Delta\mu_0$ represents the chemical potential difference of water in the hydrate-void lattice and in liquid water at $T_0$=273.15 K. $\Delta H_0$ is the corresponding enthalpy difference, $\Delta C_p$ the heat-capacity rate difference and $\Delta V$ the volume difference. Pressure $P_0$ is the vapour pressure at $T_0$; $P_0$ being much smaller than P, we use $P_0$=0.

The temperature dependence of term PV is averaged by:

$$\bar{T} = (T+273,15)/2. \quad (14)$$

$\Delta V$ and $\Delta H_0$ are both considered to be independent of the pressure. $\Delta V$ is also considered to be independent of the temperature, whereas the temperature dependence of the enthalpic term is taken into account by means of a constant heat-capacity rate difference $\Delta C_p$. The various constants that appear in Equation (13) are presented in the table hereunder:

| Properties | Units | Structure I | Structure II |
|---|---|---|---|
| $\Delta\mu_0$ | J · mol$^{-1}$ | 1264 | 883 |
| $\Delta H_0$ | J · mol$^{-1}$ | −4858 | −5201 |
| $\Delta V$ | cm$^3$ · mol$^{-1}$ | 1151 | 808 |
| $\Delta C_p$ | J · mol$^{-1}$ · K$^{-1}$ | 39.16 | 39.16 |

The combination of Equations (9) and (13) gives the final Equation (15):

$$\frac{\Delta\mu_0}{RT_0} - \int_{T_0}^{T} \frac{\Delta H_0 + \Delta C_p(T-T_0)}{RT^2} dT + \int_{P_0}^{P} \frac{\Delta V}{R\bar{T}} dP = \quad (15)$$

-continued $$\ln(\gamma x) - \sum_i v_i \ln\left(1 - \sum_k \theta_{ik}\right).$$

In this equation, the unknowns are the pressure and the temperature. We have arbitrarily decided to fix the pressure and to compute the corresponding hydrate equilibrium temperature. Seeking this temperature, i.e. solving Equation (15), is performed iteratively by means of a Newton-Raphson method starting from an initial temperature arbitrarily fixed at 0° C. We have checked that the value of this initialization does not influence the result obtained.

Validation of the Module

We have validated the program with a set of 700 experimental equilibrium points taken from 36 different bibliographic references. The results are given in form of bar graphs with the difference between the computed and the measured dissociation temperature as the abscissa and, as the ordinate, the percentage of points for which these temperature differences range between the limits shown on the bascissa. The experimental points used for these bar graphs correspond to various pressure-temperature pairs.

In FIGS. 5 to 11, we thus compare the results of the computation with experimental data in the case of various pure bodies: methane, ethane, propane, isobutane, carbon dioxide, nitrogen and hydrogen sulfide.

We observe that, for all of the pure bodies studied, the module used gives excellent predictions for the hydrate equilibrium conditions. For 99% of the points, the temperature is predicted to ±1° C. In all the cases, the maximum difference between the computed and the measured dissociation temperatures does not exceed 1.6° C.

Figure 12:
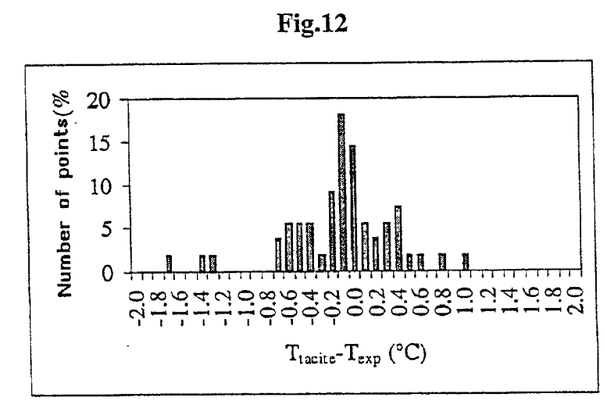
FIG. 12 shows a comparison of calculated hydrate dissociation temperatures and of experimental temperatures in the case of hydrocarbon mixtures. The bar graph is established from 55 experimental points obtained from 8 different mixtures, FIG. 13 diagrammatically shows an example of connection of a pipeline with a riser with a gas injection point (for gas lift)

The bar graph relative to the hydrocarbon, natural gas or oil mixtures data is shown in FIG. 12. The experimental data used to compute this bar graph correspond to eight different mixtures, six of natural gas type and two oils. A very good description of the behaviour of these systems by the prediction module used is again observed.

Global Simulation with or without Hydrate Appearance Risk Computation

The impact is at the level of the basic components lumping. In the standard case, one tries to optimize the number thereof so as to reduce the computing time while keeping a good representation of the equilibrium properties and of the phase properties. In cases where it is desired to predict hydrates, the composition of the components referred to as hydrate forming components has to be followed and these components should therefore not be lumped together with others.

Figure 1:
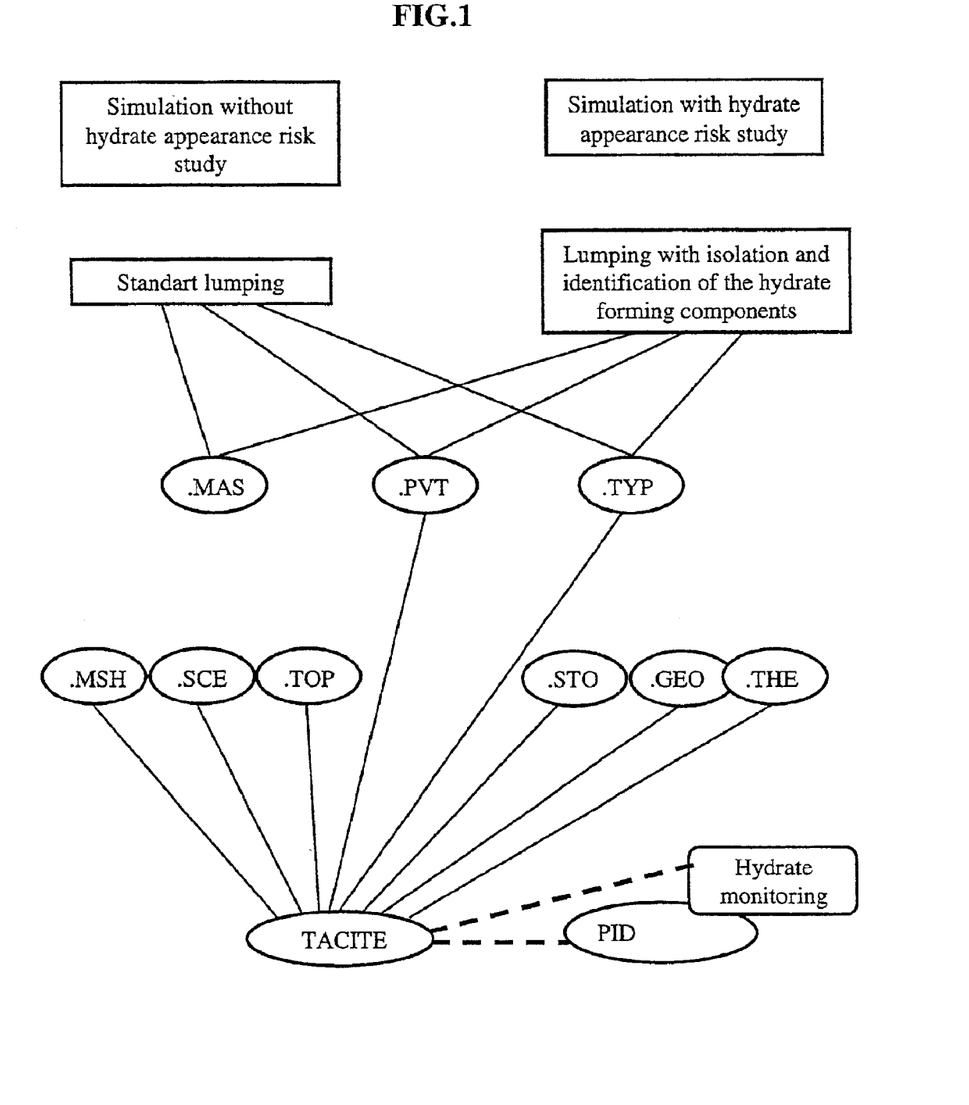
FIG. 1 shows a comparative flow chart of the simulation operations within the scope of the application of the TACITE code, according to whether the hydrate formation risk is studied or not.

Besides the data contained in <<.PVT>>, <<.MAS>> and <<.TYP>> type files, described precisely hereafter, the various input data of TACITE are recorded in 6 files (see FIG. 1)

<<.SCE>>: description of the scenario, i.e. the evolution with time of the value of the various boundary conditions (rate of inflow, outlet pressure, valve opening, . . . );

<<.TOP>>: description of the topography of the pipe (elevation of the pipe as a function of the length);

<<.GEO>>: description of the geometry of the pipe (diameter, length, porosity);

<<.THE>>: description of the thermal insulation of the pipe;

<<.MSH>>: mesh description;

<<.STO>>: description of the results file type and of the results storage frequency.

<<.PVT>> File

The <<.PVT>> file contains as many lines as there are thermodynamic fluid data, respectively:

an integer defining the type of equation of state used: 3 for Peng-Robinson or 4 for Soave-Redlich-Kwong;
an integer defining the number of phases; it is set to 1 and it is the flash module that determines their number;
the number of components;
loop on the components with indication, for each one, of their:
molar mass [kg/mol];
critical temperature [K];
critical pressure [Pa];
critical volume [m$^3$/mol];
acentric factor [-];
parachor [((N/m)$^{1/4}$m$^3$/mol)];
standard molar volume (unused);
volume correction factor [m$^3$/mol];
ideal enthalpy coefficients (table of 7 coefficients described below);
loop end;
matrix of the binary interaction coefficients [-];
calibration temperature 1 [K], calibration temperature 2 [K];
kinematic viscosity at temperature 1 [m$^2$/s], kinematic viscosity at temperature 2 [m$^2$/s].

<<.MAS>> File

This file also contains a certain number of lines indicating:
the number of initial components;
the list of the number of the group in which the corresponding initial component has been set. The order is the order in which the components were recorded in the <<.INP>> file;
the number of pseudo-components;
the various mass fractions of the components, arranged as in the <<.PVT>>file.

<<.TYP>> File

This file contains as many lines as there are pseudo-components defined in the <<.PVT>> file, and the information on the components takes account of the order in which the components are arranged in the <<.PVT>> file.

The $i^{th}$ line relates to the identifier of the nature of the $i^{th}$ component.

The following convention is selected:
If the component is neither water, nor a hydrate forming component, its type is set to 0.
If the component is hydrogen sulfide, its type is set to 1.
If the component is nitrogen, its type is set to 2.
If the component is carbon dioxide, its type is set to 3.
If the component is methane, its type is set to 4.
If the component is ethane, its type is set to 5.
If the component is propane, its type is set to 6.
If the component is isobutane, its type is set to 7.
If the component is n-butane, its type is set to 8.
If the component is water, its type is set to 9.

The TACITE simulation code uses a numerical finite-volume type solution method for simulating flows in production facilities, the pipes being discretized for example according to the gridding method described in patent application FR-EN-00/08,200 filed by the applicant.

Figure 2:
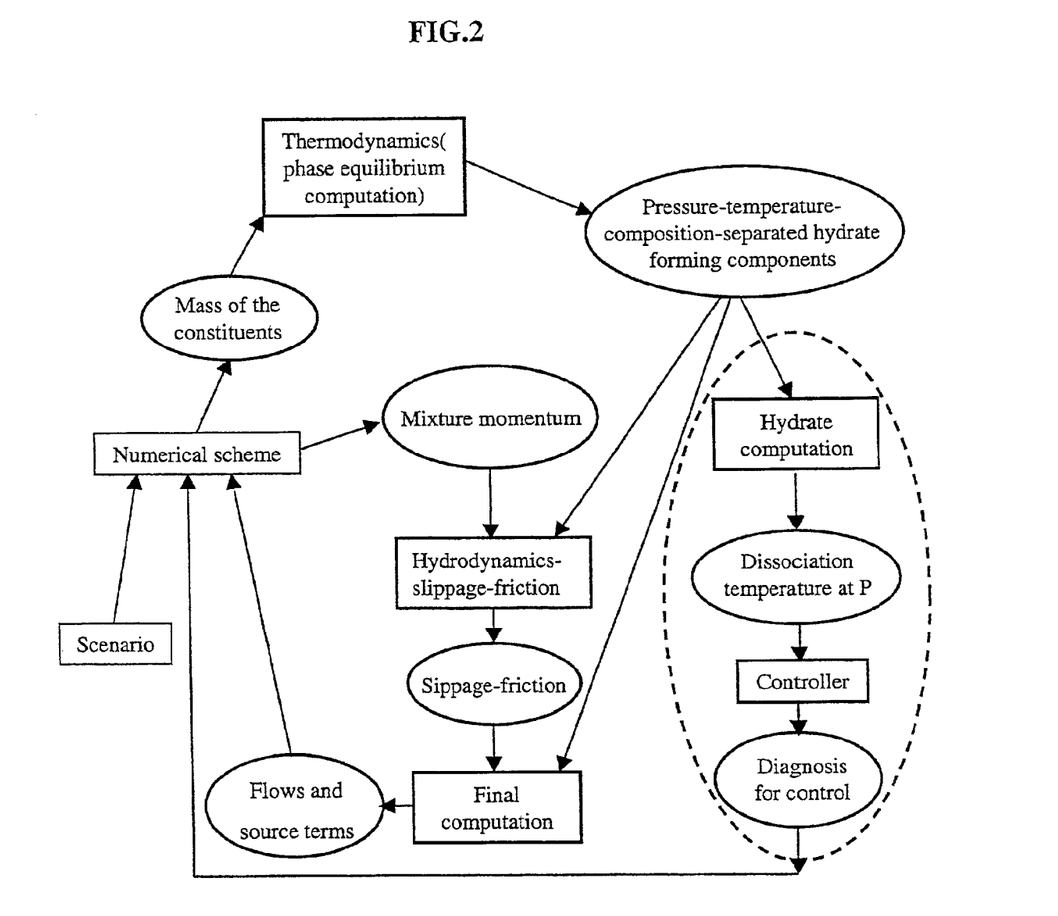
FIG. 2 shows a flow chart of the sequence of simulation operations repeated at all the points of a pipeline grid pattern, FIG. 3 diagrammatically shows a control mode that can be applied for any operation intended to fight hydrate formation.

At any time, at any point of the grid, the modelling computations are carried out according to the flow chart of FIG. 2.

The numerical scheme is supplied by the flow terms and the source terms, the change in the boundary conditions (scenario).

The numerical scheme provides the mass of the constituents, the momentum of the mixture, the internal energy of the mixture (non-isothermal).

Knowing the masses and the energy gives, by means of the thermodynamic flash, the pressure, the temperature and the mass composition of the phases at equilibrium.

Figure 3:
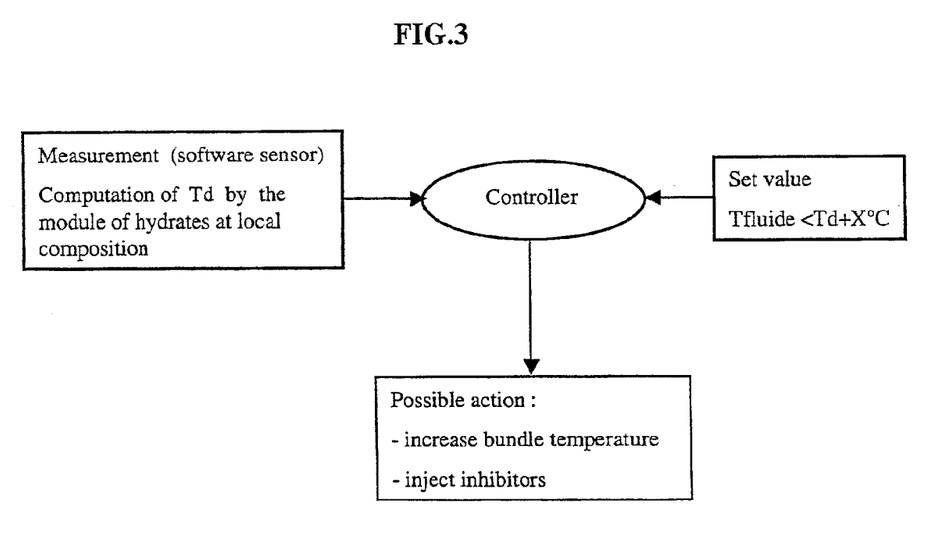

Knowing the pressure and the mass composition, it is possible, if the user wishes to (see part surrounded with a dotted line), to:

precisely compute, by means of the hydrate prediction module, the hydrate dissociation temperature Td (temperature below which, if hydrates have formed, they cannot dissociate)

use a PID type controller C (FIG. 3) to compare the calculated temperature of the fluid (Tfluid) and this dissociation temperature Td and take action if this fluid temperature is lower than the dissociation temperature increased by a slight difference (to anticipate the possible problems) by means of one of the control means provided.

Apart from this possible control, computation continues, knowledge of the mixture equilibrium and of the phase properties, associated with the knowledge of the momentum of the mixture allows, by means of the hydrodynamic module, to provide the slippage between the phases and the wall and interface frictions.

It is then possible to compute the source terms and the flows for the next computation.

On-Line Control

Hydrate formation control operations are generally very costly. Fine modelling as allowed by the method according to the invention allows the operator to permanently know the thermodynamic conditions prevailing all along the pipeline and thus to determine the points where hydrates are likely to form. He can then, if the need arises and only then, take action to fight hydrate deposition. This necessity is more particularly critical in case of temporary production stop or when gas is injected into the circulating mixture (gas lift) for example.

Figure 4:
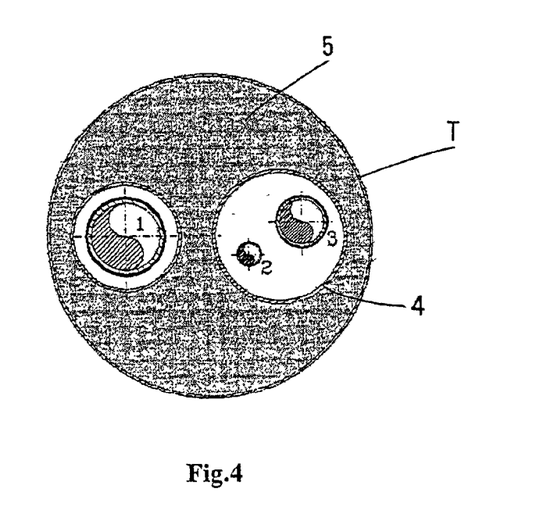
FIG. 4 shows the cross-section of a tube along which several series of fluid circulation lines or tubes are arranged.
Figure 5:
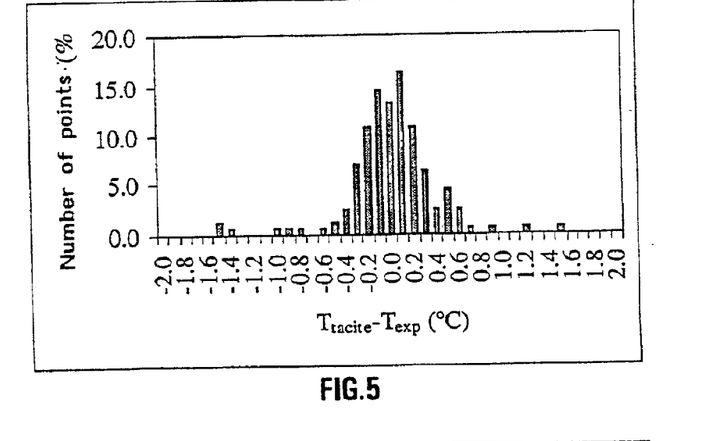
FIG. 5 shows a comparison of calculated hydrate dissociation temperatures and of experimental temperatures in the case of methane. The bar graph is established from 158 experimental points.
Figure 6:
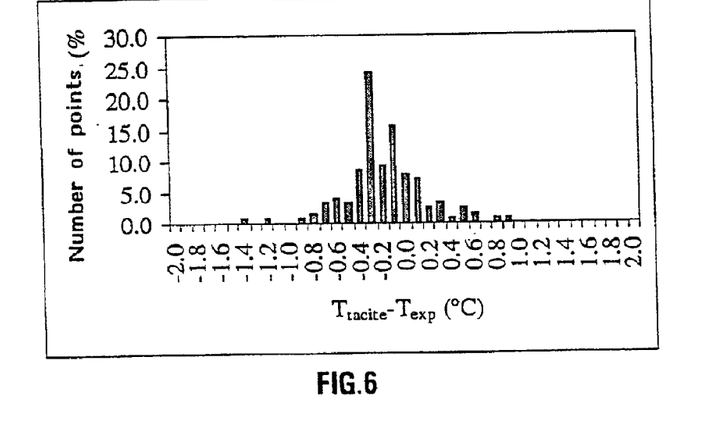
FIG. 6 shows a comparison of calculated hydrate dissociation temperatures and of experimental temperatures in the case of ethane. The bar graph is established from 126 experimental points.
Figure 7:
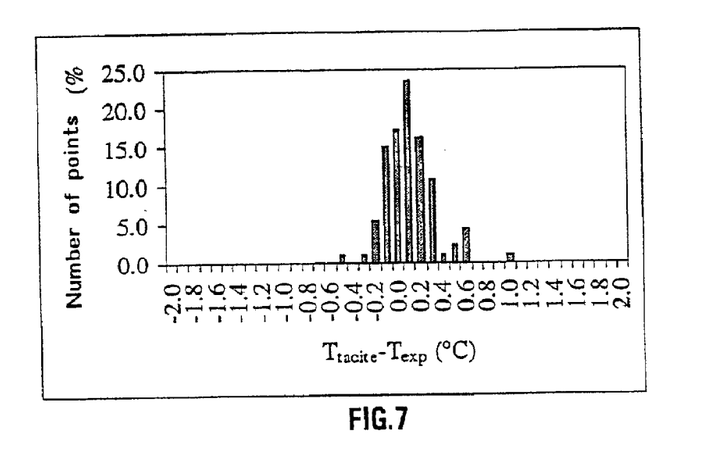
FIG. 7 shows a comparison of calculated hydrate dissociation temperatures and of experimental temperatures in the case of propane. The bar graph is established from 93 experimental points.
Figure 8:
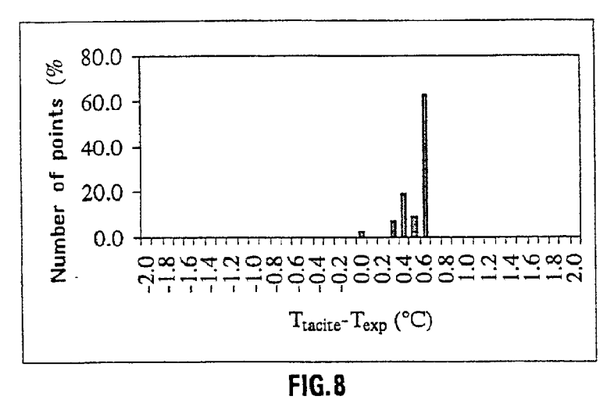
FIG. 8 shows a comparison of calculated hydrate dissociation temperatures and of experimental temperatures in the case of isobutane. The bar graph is established from 43 experimental points.
Figure 9:
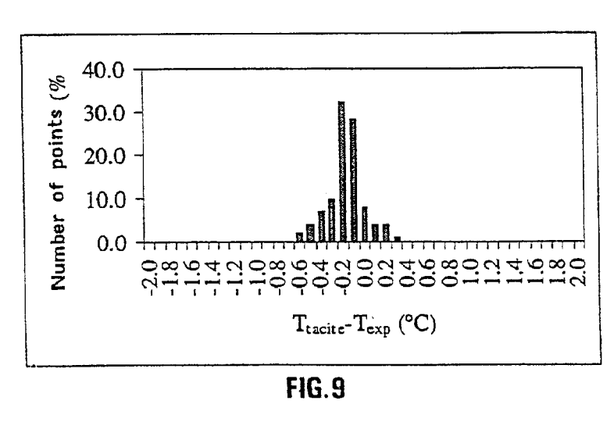
FIG. 9 shows a comparison of calculated hydrate dissociation temperatures and of experimental temperatures in the case of carbon dioxide. The bar graph is established from 102 experimental points.
Figure 10:
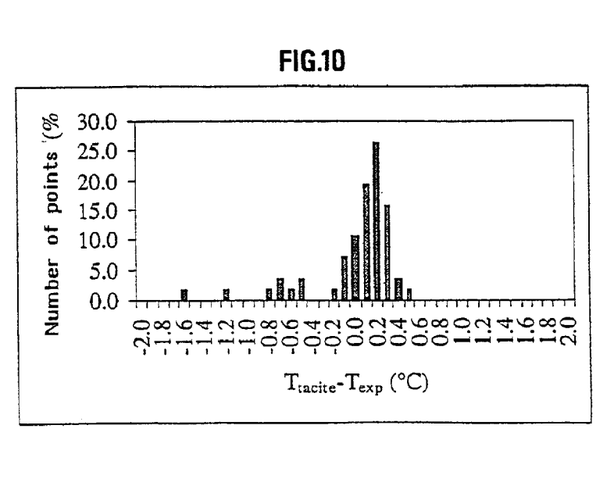
FIG. 10 shows a comparison of calculated hydrate dissociation temperatures and of experimental temperatures in the case of nitrogen. The bar graph is established from 57 experimental points.
Figure 11:
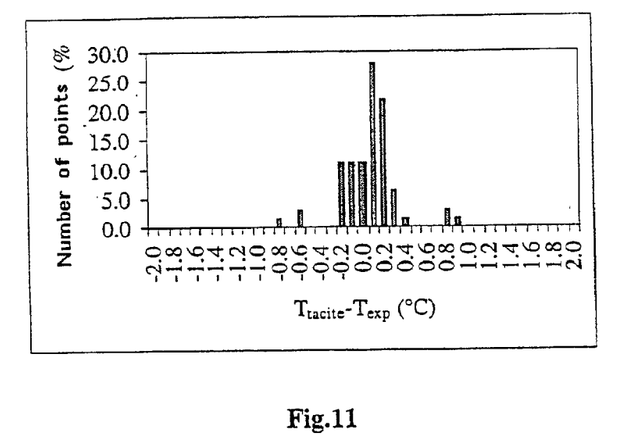
FIG. 11 shows a comparison of calculated hydrate dissociation temperatures and of experimental temperatures in the case of hydrogen sulfide. The bar graph is established from 64 experimental points.

A first mode of taking action consists in heating the circulating fluids so as to bring them above the predicted hydrate dissociation temperature, at least at the points of the pipe where the risk has appeared. The oil lines used for deep-sea marine production are generally included with other lines in a metal pipe T externally coated with an insulating layer. This set of lines, referred to as bundles by the man skilled in the art, is often distributed in several bundles such as F1, F2 (see FIG. 4). Each bundle generally comprises one or more transport lines 1, 2, 3 for single-phase or multiphase fluids which can be arranged in a common tube 4 possibly also externally coated with an insulating layer. The inside of each tube 4 is in most cases filled with a single-phase fluid. The inner space of pipe T, between the various bundles F1, F2, is filled for example with a thermally insulating foam 5. One of transport lines 2, 3 can be used for example to circulate a heating fluid if need be.

One can for example refer to the following publication for modelling of the heat transfers between the oil pipes of all the lines and their environment (other lines, outside medium) by taking account of the interposed thermal insulation means:

Duret, E. et al., <<Pipeline bundles model implemented into a multiphase flow model>>, SPE 62948, SPE Annual Technical Conference and Exhibition, Dallas, Tex., Oct. 1–4, 2000.

A second mode of taking action consists in injecting into the fluids inhibiting additives of a well-known type that prevent hydrate formation.

This control system is not based on a measurement provided by a real sensor but on a measurement provided by a sensor referred to as <<software>> sensor.

Interest of a Compositional Code for a Hydrate Computation

Figure 13:
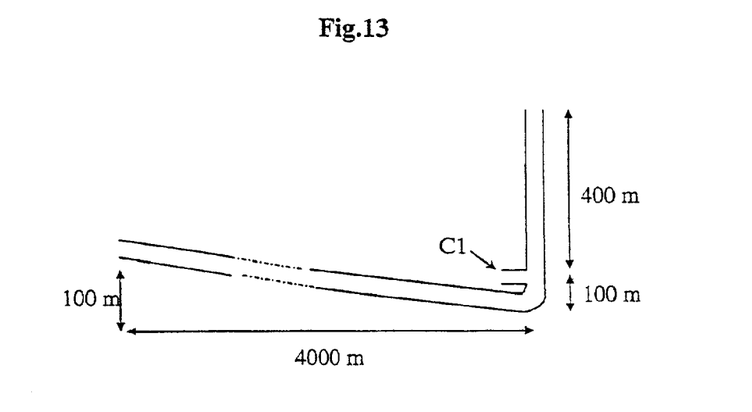

Using a compositional code such as the TACITE code allows exact computation, at any point of the pipeline, at the calculated pressure of the fluid and for the local composition calculated during simulation, of the hydrate dissociation temperature and consequently much better simulation of the hydrate appearance risks than with codes where the composition is assumed to be fixed, corresponding to the composition injected at the pipe inlet. It has been possible to observe, for example, that gas injection at the foot of a riser (a technique well known to the man skilled in the art) modifies the local thermodynamic conditions of a given mixture of petroleum fluids, so much so that hydrate formation could be predicted, whereas when assuming a fixed composition of the mixture, this risk is in no way detected. We illustrate this point with the simulation of a gas injection at the foot of a riser connected to a pipeline as shown in FIG. 13, supplied with a mixture whose composition is given in the table hereunder.

| Components | Composition (% by mole) |
|---|---|
| $C_1$ | 10.53 |
| $C_2$ | 2.64 |
| $C_3$ | 2.63 |
| $iC_4$ | 2.63 |
| $nC_4$ | 2.63 |
| $iC_5$ | 2.63 |
| $nC_5$ | 2.63 |
| $nC_{10}$ | 13.16 |
| $nC_{20}$ | 7.90 |
| $H_2O$ | 52.62 |

The simulation is carried out considering that the initial mixture has been modified by injection, at the bottom of the riser, of methane favouring hydrate formation.

Figure 14:
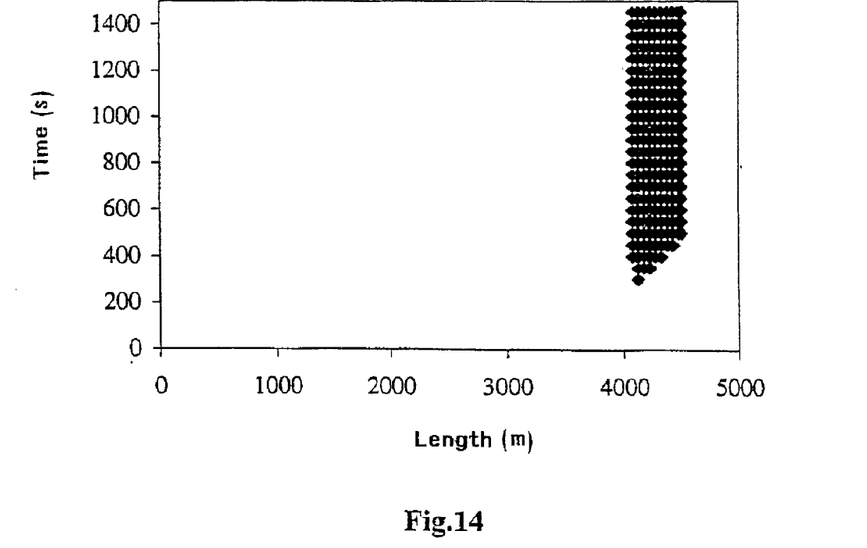
FIG. 14 shows, in a two-dimensional pipe length-time diagram, an example of a domain that can be calculated by means of the hydrate appearance method with the layout of FIG. 13.

In a pipe length-time diagram, the hydrate appearance domain obtained is shown in FIG. 14.

Figure 15:
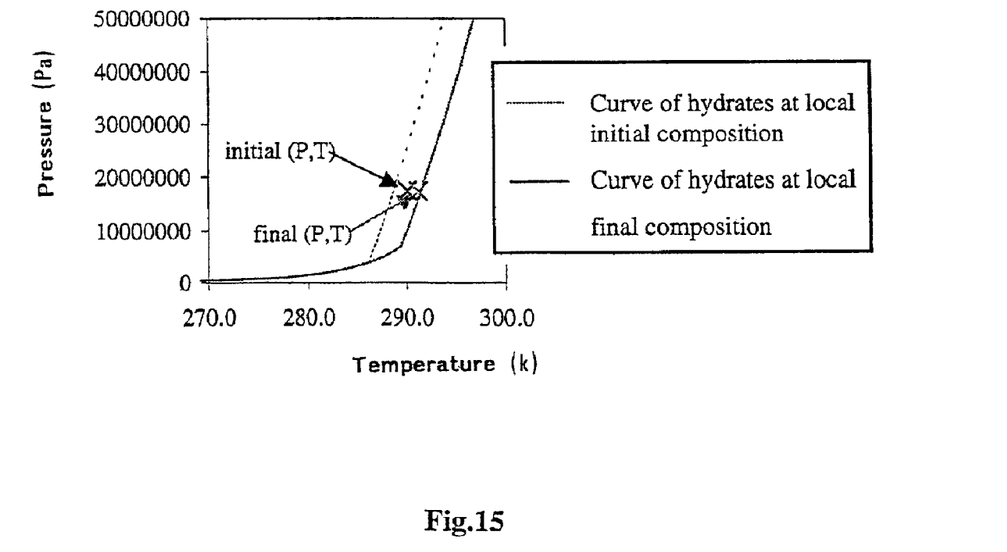
FIG. 15 shows, in a two-dimensional pressure-temperature diagram, two local curves of hydrate appearance in the pipes, according to whether a change in the composition of the circulating mixture is taken into account or not.

We have computed and shown in the two-dimensional pressure-time diagram of FIG. 15 two local hydrate formation curves, one (in dotted line) considering that the composition has not been altered by the injection of methane, as would be the case with a non-compositional simulation code, the other (in full line) taking account of the composition change that has occurred.

It can be easily checked in FIG. 15 that the point representing the pressure-temperature pair in the end would be wrongly considered to be without risks since it is on the right of the hydrate curve calculated at the initial composition. The hydrate appearance risk domain shown in FIG. 14 would also be modified because of the composition variations.

What is claimed is:

1. A method for continuous control of hydrate formation at any point of a pipe carrying a multiphase mixture of petroleum fluids, using a mechanistic hydrodynamic module and an integrated compositional thermodynamic module to define the phase properties, and applying mass conservation and momentum conservation equations, as well as equations of energy transfer in the mixture, considering that the multiphase mixture is substantially continuously at equilibrium, a composition of the multiphase mixture is variable all along the pipe and a mass of each constituent of the mixture is globally defined by a mass conservation equation regardless of phase state thereof, and the petroleum fluids are grouped together into a limited number of pseudo-components, comprising:

a) detecting hydrate formation conditions by:
      carrying out a grouping of the petroleum fluids into selected pseudo-components so as to isolate the hydrate forming components, with a definition for each pseudo-component of a mass fraction and of a number of characteristic physical quantities, and
      by applying to said modules data relative to these particular pseudo-components so as to determine a hydrate dissociation temperature;
   b) determine at any point along said pipe, a temperature of said mixture of petroleum fluids;
   c) using a control device to compare said temperature of the petroleum fluids with said hydrate dissociated temperature ; and
   d) applying measures intended to control hydrate formation under said control device.

2. A method as claimed in claim 1, characterized in that heating means associated with pipe are used to raise the temperature of the petroleum fluids above the dissociation temperature.

3. A method as claimed in claim 2, characterized in that, pipe being included with at least a second pipe in a tube isolated from the outside medium, second pipe is used for circulation of a warm fluid.

4. A method as claimed in claim 1, characterized in that hydrate inhibitors are injected into pipe under the control of control device.

5. A method for continuous detection of thermodynamic hydrate formation at conditions, any point of a pipe carrying a multiphase mixture of petroleum fluids, using a mechanistic hydrodynamic module and an integrated compositional thermodynamic module to define the phase properties, and applying mass conservation and momentum conservation equations, as well as equations of energy transfer in the mixture, considering that the multiphase mixture is substantially continuously at equilibrium, a composition of the multiphase mixture is variable all along the pipe and a mass of each constituent of the mixture is globally defined by a mass conservation equation regardless of phase state thereof, and the petroleum fluids are lumped together into a limited number of pseudo-components, comprising:

carrying out a lumping of the petroleum fluids into selected pseudo-components so as to isolate the hydrate forming components, with a definition for each pseudo-component of a mass fraction and of a number of characteristic physical quantities; and
   applying to said modules data relative to these particular pseudo-components so as to determine at any point along said pipe a hydrate dissociation temperature.

* * * * *